US00PP16081P2

(12) United States Plant Patent
Yates

(10) Patent No.: US PP16,081 P2
(45) Date of Patent: Nov. 1, 2005

(54) ***ANTIRRHINUM* PLANT NAMED 'YACOY'**

(50) Latin Name: *Antirrhinum majus*
Varietal Denomination: YACOY

(76) Inventor: Frederic Yates, The Orchard, Sumerford, Holmes Chapel, Congleton, Cheshire (GB), CW12

( * ) Notice: Subject to any disclaimer, the term of this patent is extended or adjusted under 35 U.S.C. 154(b) by 66 days.

(21) Appl. No.: 10/883,837

(22) Filed: Jul. 6, 2004

(51) Int. Cl.[7] ..... A01H 5/00
(52) U.S. Cl. ..... Plt./322
(58) Field of Search ..... Plt./322

*Primary Examiner*—Anne Marie Grunberg
*Assistant Examiner*—June Hwu

(57) ABSTRACT

A new cultivar of *Antirrhinum* plant named 'YACOY' that is characterized by fragrant, large orange and yellow flowers, mounding habit, and green foliage. In combination these traits set 'YACOY' apart from all other existing varieties of *Antirrhinums* known to the inventor.

2 Drawing Sheets

Genus: *Antirrhinum*. Species: *majus*.
Denomination: YACOY.

BACKGROUND OF THE INVENTION

The present invention relates to a new and distinct cultivar of snapdragon, known botanically as *Antirrhinum majus* and referred to hereinafter by the cultivar name 'YACOY'.

'YACOY' was selected by the inventor, in 2000, from a formal breeding program conducted in a cultivated area of Congleton, Cheshire, England. The breeding program was conducted by the inventor and established in 1990, the objective being to select cultivars of snapdragons that exhibit new flower colors along with new and improved growth habits.

'YACOY' is of hybrid origin and resulted from the induced cross-pollination of female and male parent seedlings. The female parent is an unnamed plant of the species *Antirrhinum majus* (unpatented) and the male parent is an unnamed *Antirrhinum* (unpatented) derived from open pollination. The female parent plant exhibits a semi-trailing habit. The male parent exhibits an upright habit. 'YACOY' differs from the female parent plant in flower color, internode length and habit. 'YACOY' differs from the male parent in flower color. 'YACOY' exhibits a mounding habit along with large orange and yellow flowers that distinguish it from all other *Antirrhinum* known to the inventor. The closest comparison plants are *Antirrhinum* 'Lemon Blush Chandelier' (unpatented) and *Antirrhinum* 'Rose Pink Chandelier' (unpatented). 'YACOY' is distinguishable from the comparison plants by mounding habit and orange and yellow flower color.

The first asexual propagation was conducted in June of 2000 by the inventor in Congleton, Cheshire, England. The method of propagation used was tip cuttings. Since that time the unique characteristics of 'YACOY' have been found stable in successive generations.

SUMMARY OF THE INVENTION

The following traits have been repeatedly observed and represent the characteristics of the new *Antirrhinum* cultivar 'YACOY'. These traits in combination distinguish this cultivar from all other commercial varieties known to the inventor. 'YACOY' has not been tested under all possible conditions and phenotypic differences may be observed with variations in environmental, climatic, and cultural conditions.

1. *Antirrhinum* 'YACOY' exhibits a mounding habit.
2. *Antirrhinum* 'YACOY' exhibits short internodes.
3. *Antirrhinum* 'YACOY' exhibits large orange and yellow flowers.
4. *Antirrhinum* 'YACOY' is propagated by tip cuttings.
5. *Antirrhinum* 'YACOY' is 25 cm. in height and 35 cm. in width at maturity.
6. *Antirrhinum* 'YACOY' is suitable for use as a container or patio plant.
7. *Antirrhinum* 'YACOY' is hardy to 10° Centigrade.

BRIEF DESCRIPTION OF THE DRAWINGS

The accompanying color drawings illustrate the overall appearance of the new cultivar 'YACOY' showing the colors to be as true as is reasonably possible to obtain, in colored reproductions of this type. Colors in the drawings may differ from the color values cited in the detailed botanical description, which accurately describe the actual colors of the new variety 'YACOY'.

The drawing labeled as FIG. 1 illustrates the plant from a side perspective.

Figure 1:
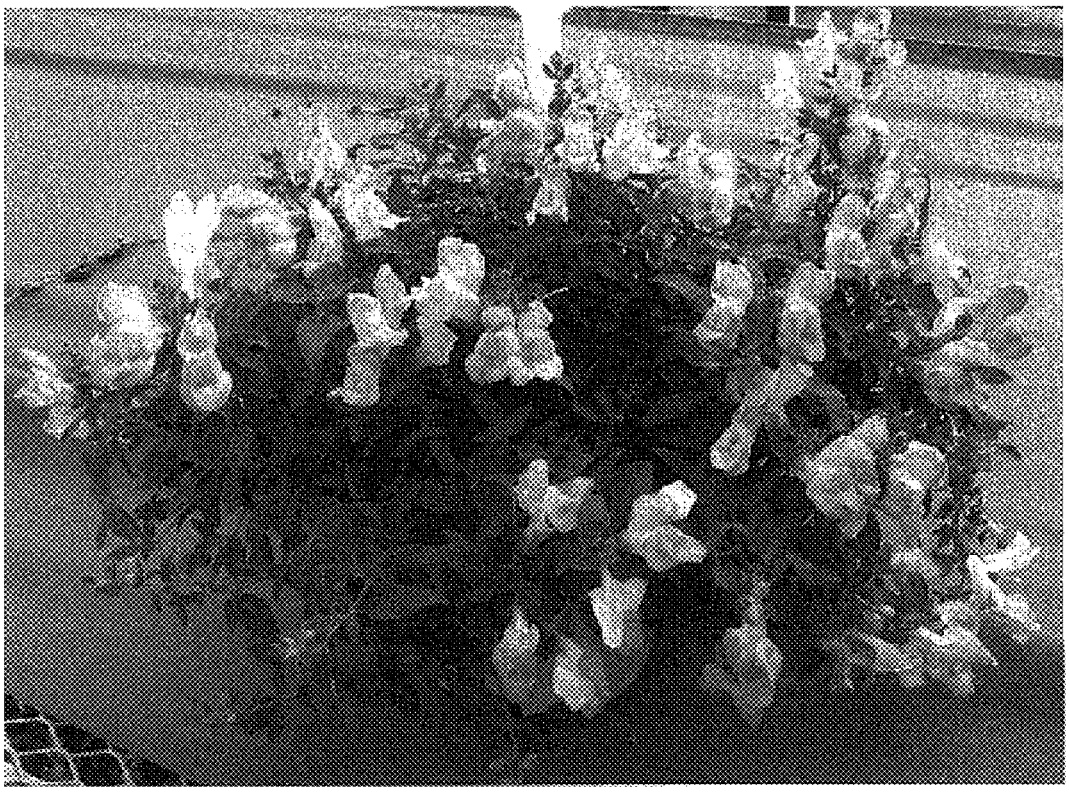
Figure 2:
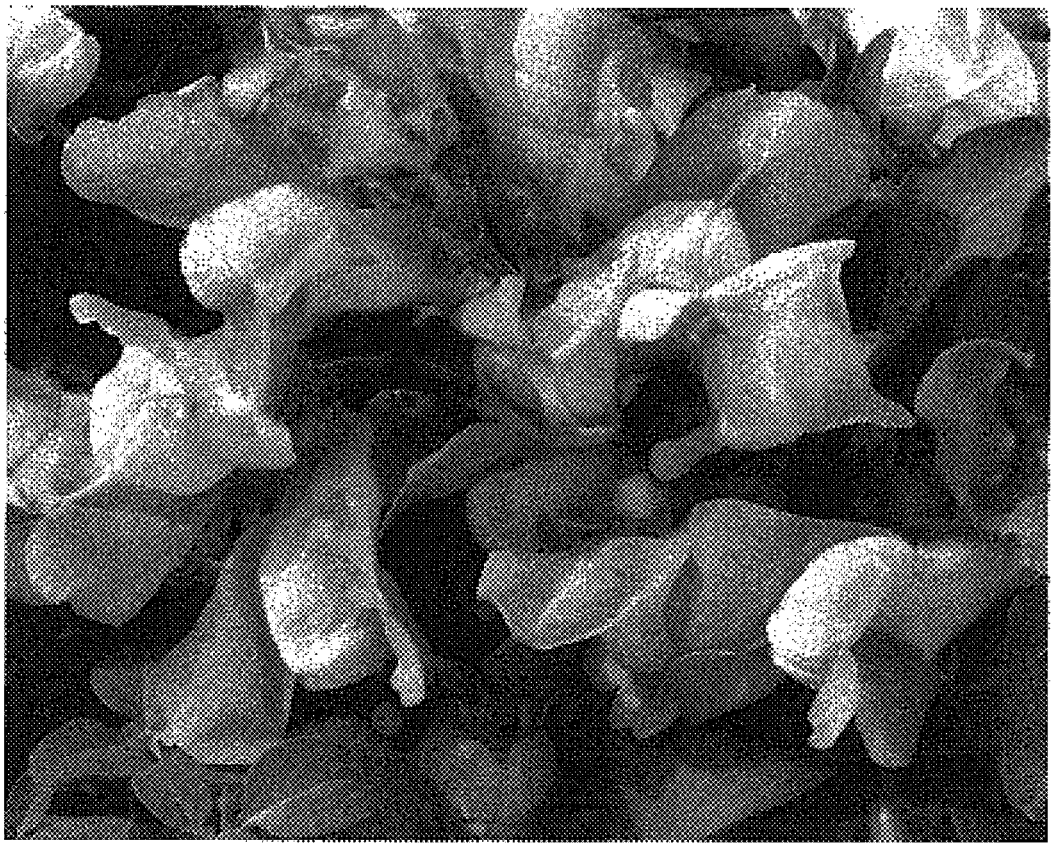

The drawing labeled as FIG. 2 illustrates a close-up view of the flower. The drawings were made using conventional photographic techniques and although foliage color may appear different from actual colors due to light reflectance, they are as accurate as possible by conventional photography.

BOTANICAL DESCRIPTION OF THE PLANT

The following is a detailed description of the new cultivar 'YACOY' as grown in a one-liter container under greenhouse conditions in Encinitas, Calif. Phenotypic differences may be observed with variations in environmental, climatic, and cultural conditions. The color determinations are in accordance with The Royal Horticultural Society Colour Chart (2001) except where general color terms of ordinary dictionary significance are used. There are no special growing requirements or growing problems known to the inventor.

Botanical classification: *Antirrhinum* 'YACOY'.
Species: *majus*.
Common name: Snapdragon.
Use: Container or patio plant.
Parentage: 'YACOY' is a hybrid plant that resulted from induced cross-pollination of the female and male parent plants. The male and female parents are unintroduced *Antirrhinum* hybrids from the inventors breeding program.
*Female parent plant.*—*Antirrhinum majus.*
*Male parent plant.*—Unnamed *Antirrhinum* hybrid.
Propagation: Tip cuttings.
Vigor: Vigorous.
Type: Annual.
Plant dimensions: 16 cm. in height and 28 cm. in width in a one-liter container.
Quantity of flowers: 25 flowers on a one-litre container plant.
Quantity of buds: 30 buds on a one liter-container plant.
Root system: Fibrous.
Diseases and pests: No known pests or diseases.
*Plant habit.*—Mounding.
*Cropping time.*—8 weeks are needed to produce a finished commercial 4-inch container.
*Time to develop roots.*—10 days are needed to develop roots on an initial cutting.
*Temperature to develop roots.*—17–20° Centigrade.
*Seasonal interest.*—Flowers in winter, spring and summer.
*Hardiness.*—10° Centigrade.
*Sunlight requirements.*—Normal.
*Soil requirements.*—Free-draining nursery compost or peat.
Stem:
*Stem shape.*—Cylindrical.
*Stem color.*—144B.
*Stem dimensions.*—6–7 cm in length by 2 mm in diameter.
*Internode length.*—1.25 cm between nodes.
*Stem surface.*—Glabrous.
*Branching habit.*—Basal branching.
Foliage:
*Leaf arrangement.*—Opposite.
*Leaf division.*—Simple.
*Shape.*—Lanceolate.
*Base.*—Cuneate.
*Apex.*—Acute.
*Venation pattern.*—Parallel with one prominent midvein.
*Vein color* (*abaxial and adaxial surfaces*).—138B.
*Margins.*—Entire.
*Leaf surfaces* (*abaxial and adaxial*).—Glabrous.
*Leaf color* (*adaxial surface*).—137B.
*Leaf color* (*abaxial surface*).—138B.
*Leaf dimensions* (*mature leaves*).—4 cm. in length and 1.25 cm in width.
*Leaf dimensions* (*young leaves*).—9 mm. in length and 6 mm. in width.
*Leaf fragrance.*—Grass-like.
*Attachment.*—Petiolate to sessile.
*Petiole shape.*—Oval in cross section.
*Petiole dimensions* (*mature leaves*).—6 mm in length and 1.5 mm. in width.
*Petiole dimensions* (*young leaves*).—4 mm. in length and 1 mm. in width.
*Petiole color.*—138B.
*Petiole surface.*—Pubescent.

Flower:
*Inflorescence.*—Terminal raceme.
*Flower type.*—Solitary in leaf axis.
*Aspect.*—Outward and upward.
*Flower shape.*—Bilabiate.
*Flower dimensions.*—4 cm. in height, 3 cm. in depth and 2.75–3 cm. in width.
*Flower color.*—13A, 43C and 185D are each individually present.
*Bud shape.*—Obovate.
*Bud color.*—42A.
*Bud dimensions.*—Bud dimensions range from 1.25 cm. in length and 0.50 cm. in width, to 1.75 cm. in length and 1 cm. in width.
*Bud surface.*—Pubescent.
*Number of lips.*—Two.
*Upper lip dimensions.*—1.50 cm. in height and 3.75 cm. in width.
*Lower lip dimensions.*—2 cm. in height and 3 cm. in width.
*Palate dimensions.*—1.50 cm. in width and 1.50 cm. in height.
*Palate surfaces* (*outside*).—Glabrous.
*Palate surface* (*underside*).—Pubescent.
*Lobes* (*upper lip*).—Two erect lobes.
*Lobes* (*lower lip*).—Three spreading lobes.
*Margins* (*upper lip*).—Slightly ruffled.
*Margins* (*lower lip*).—Slightly ruffled.
*Palate color.*—13A.
*Lip surfaces* (*upper and lower*).—Glabrous.
*Upper lip color* (*adaxial surface*).—43C and 13A are both individually present on an individual flower.
*Upper lip color* (*abaxial surface*).—185D.
*Lower lip color* (*adaxial surface*).—43C.
*Lower lip color* (*abaxial surface*).—185D.
*Corolla tube mouth.*—Closed at mouth and saccate at base.
*Corolla tube surfaces* (*inside and outer surfaces*).—Glabrous.
*Corolla tube color* (*inside surface*).—155B.
*Corolla tube color* (*outer surface*).—43C.
*Corolla tube depth.*—2.50 cm. in depth.
*Flowering season.*—Winter, spring and summer.
*Flowering time.*—Diurnal.
*Pedicel dimensions.*—8 mm. in length and 1.5 mm. in width.
*Pedicel shape.*—Cylindrical.
*Pedicel surface.*—Pubescent.
*Pedicel color.*—138B.
*Calyx color.*—138B.
*Number of sepals.*—Five sepals in number.
*Sepal color* (*adaxial and abaxial surfaces*).—138B.
*Sepal surface.*—Pubescent.
*Sepal shape.*—Ovate.
*Fused or unfused.*—Basally fused.
*Sepal dimensions.*—7 mm. in length and 4 mm. in width.
*Sepal apex.*—Acute.
*Flower fragrance.*—Sweet candy fragrance.
Reproductive organs:
*Nectary surface* (*underside of palate*).—Lanate.
*Nectary color.*—2C.
*Stamens.*—4 in number.
*Stamen shape.*—Filament.
*Stamen color.*—N155B.

*Stamen dimensions.*—Two are 17 mm. in length and 1 mm. in width, and two are 15 mm. in length and 1 mm. in width.
*Anther dimensions.*—3 mm. in length and 2 mm. in width.
*Anther shape.*—Oval.
*Anther color.*—7 A.
*Quantity of pollen.*—Large amount.
*Color of pollen.*—7A.
*Pistil.*—One in number.
*Pistil color.*—N155B.
*Pistil dimensions.*—15 mm. in length and 1 mm. in width.
*Pistil shape.*—Club shaped.
*Stigma dimensions.*—3 mm. in length and 2 mm. in width.
*Stigma color.*—149A.
*Ovary position.*—Superior.
*Ovary color.*—149A.
*Ovary shape.*—Cone shaped.
*Ovary dimensions.*—2 mm. in length and 3 mm. in width.
*Ovary surface.*—Mesic.

Seed: No seed observed to date.

It is claimed:

1. A new and distinct cultivar of *Antirrhinum* plant named 'YACOY' as described and illustrated.

* * * * *